United States Patent [19]

Kirkley

[11] 4,335,715
[45] Jun. 22, 1982

[54] OSTEOTOMY GUIDE

[76] Inventor: William H. Kirkley, 241 Coventry Rd., Decatur, Ga. 30050

[21] Appl. No.: 161,553

[22] Filed: Jun. 20, 1980

[51] Int. Cl.$^3$ .......................... A61F 5/04; A61B 17/18
[52] U.S. Cl. ............................... 128/92 EB; 128/92 A
[58] Field of Search ................ 128/92 A, 92 EB, 305, 128/303 B

[56] References Cited

U.S. PATENT DOCUMENTS

| | | | |
|---|---|---|---|
| 2,371,519 | 3/1945 | Haynes | 128/92 A |
| 2,666,430 | 1/1954 | Gispert | 128/92 EB |
| 3,941,123 | 3/1976 | Volkov et al. | 128/92 A |
| 4,150,675 | 4/1979 | Comparetto | 128/305 |
| 4,185,623 | 1/1980 | Volkov et al. | 128/92 A |

OTHER PUBLICATIONS

Clinical Orthopaedics & Related Research, Oct. 1975, "A Jig for Pin Insertion in the Performance of High Tibial Osteotomy", No. 112, pp. 242–244, by Lippert et al.

Primary Examiner—Lee S. Cohen
Assistant Examiner—C. W. Shedd
Attorney, Agent, or Firm—George M. Thomas

[57] ABSTRACT

A pair of guide blocks are movable along an arcuate track of a substantially constant radius and each defines at least one rectilinear pin opening therethrough which extends parallel to the radius of the arcuate track for receiving rectilinear alignment pins therethrough. A scale extends along the arcuate track which indicates the angle of orientation of the pins with respect to each other. A first pin is inserted into a bone, a pin opening of one of the guide blocks is inserted about the protruding end of the first pin, and a second pin is inserted through the pin opening of the other guide block and then into the bone at an angle with respect to the first pin which corresponds to the angle indicated on the arcuate track. After the pins have been inserted into the bone, the osteotomy guide is removed from the pins, the bone is severed, and the bone segments are adjusted until the protruding ends of the pins are in alignment with each other.

6 Claims, 15 Drawing Figures

U.S. Patent   Jun. 22, 1982   Sheet 1 of 3   4,335,715
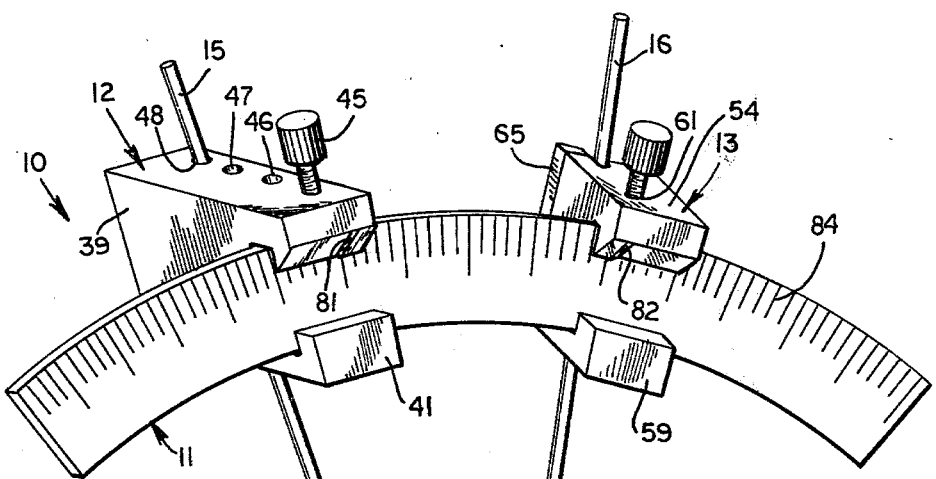
Fig_1
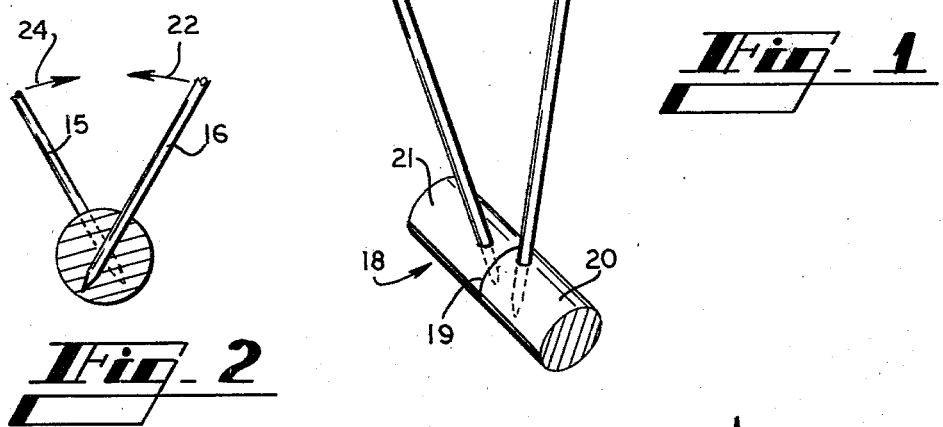
Fig_2
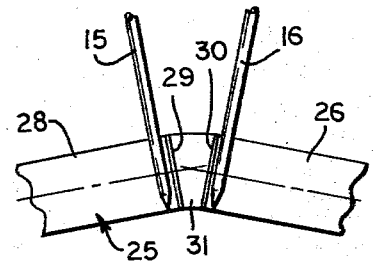
Fig_3
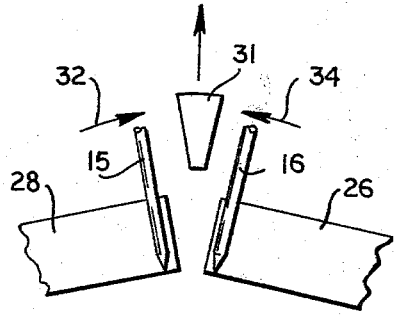
Fig_4

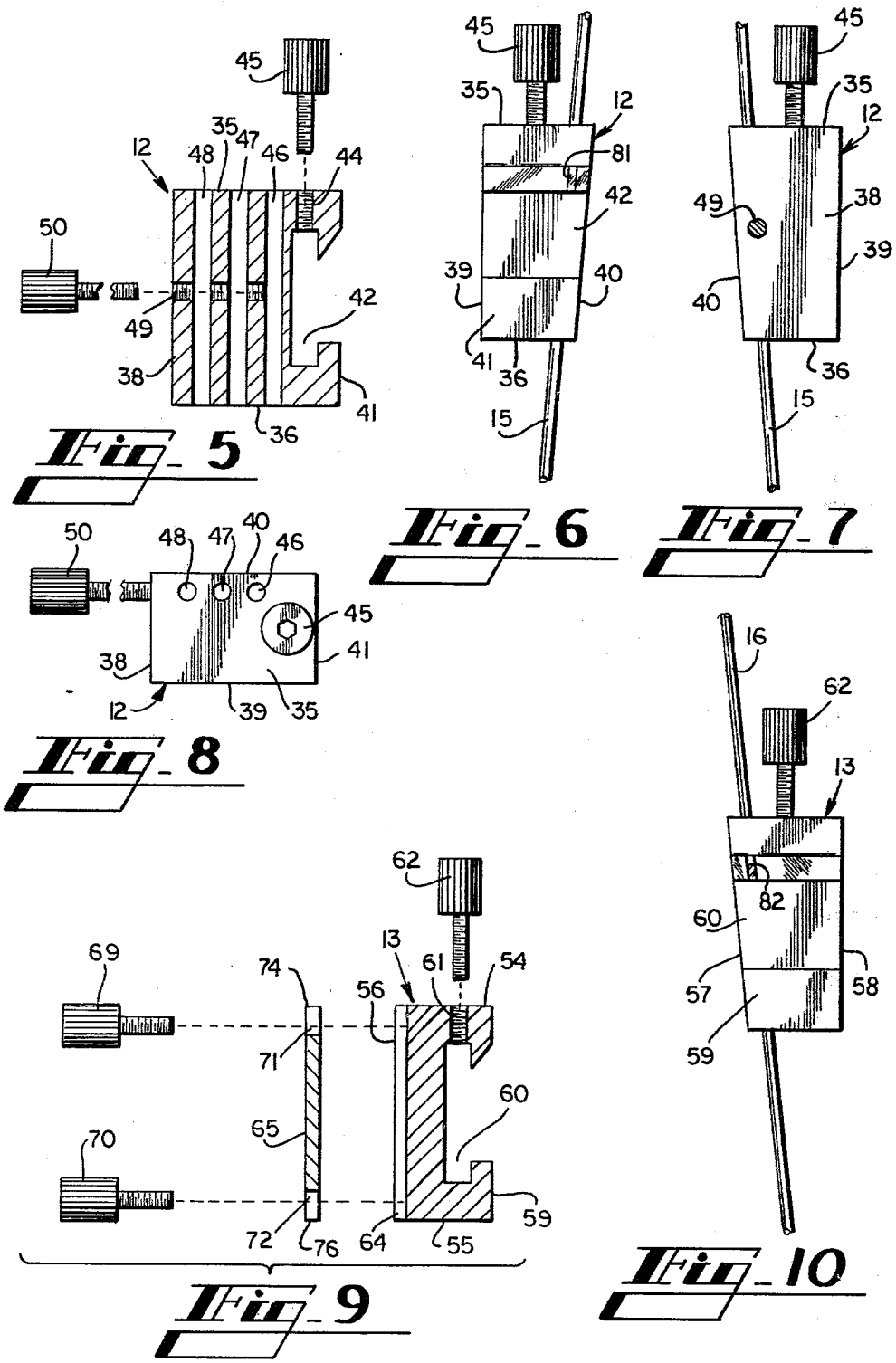

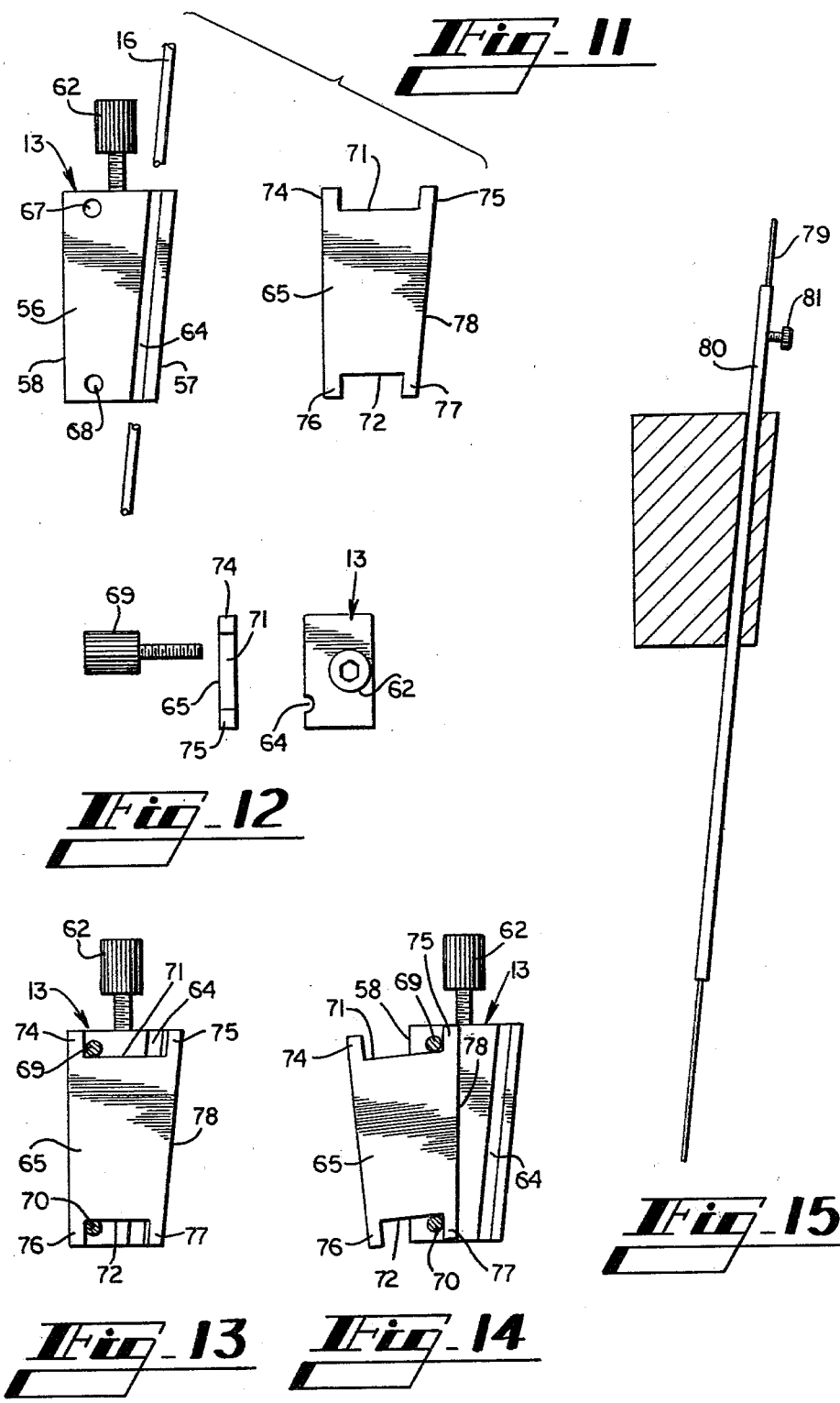

OSTEOTOMY GUIDE

BACKGROUND OF THE INVENTION

This invention relates to an osteotomy guide which assists the orthopedic surgeon in aligning the segments of bones in a procedure for correcting a bone deformity, wherein pins are inserted into the bones at an angle with respect to each other which corresponds to the desired angle of correction of the bone.

When a bone of the human body is incorrectly formed, as by being twisted or "rotated" along its longitudinal axis or by having an angular deformity therein, a procedure for correcting the deformity is to sever the bone and reconnect the segments in proper orientation with respect to each other. In the instance of a rotational deformity, the correcting procedure includes the steps of severing the bone into two segments and twisting or "derotating" the segments with respect to each other, and then connecting the segments back together in their correct alignment. In the instance of a bone having an improper angle formed therein the correcting procedure includes the steps of severing the bone in two locations on opposite sides of the angle in the bone to form a small wedge shaped segment of bone which has the same angle as the deformity of the bone, removing the wedge of bone and reorienting the remaining segments in alignment and connecting the segments together.

While it is usually a simple matter to perceive the desired angle of correction for a malformed bone, the orthopedist must cut through the malformed bone and adjust the bone segments with respect to each other to correct the deformity. The correction procedure is difficult in that the orthopedist usually encounters some difficulty in correctly aligning and maintaining the alignment of the bone segments during the operation. For example, if a bone is to be derotated it is difficult to perceive the exact angle through which the bone has been derotated, and it is also difficult to maintain the proper angle of derotation during the reconnection procedure for the bone segments.

SUMMARY OF THE INVENTION

Briefly described, the present invention comprises an osteotomy guide for assisting the orthopedist in correctly aligning severed bone segments in a procedure for correcting a boney deformity, either an angular deformity or a rotational deformity. The guide includes an arcuate track of a substantially constant radius and a pair of guide blocks movable along the length of the arcuate track. Each of the guide blocks defines at least one rectilinear pin opening therethrough, and the pin openings extend parallel to the radius of the arcuate track and receive rectilinear alignment pins therethrough. A scale is imposed on the arcuate track and indicates the angles thereabout with respect to the center of the radius of curvature of the arcuate track. The surgeon places the guide blocks on the arcuate track at an angle from each other which corresponds to the desired angle of correction of the bone. A first alignment pin is then inserted through the bone adjacent the position where the correction is to be made. One of the guide blocks which is mounted on the arcuate track is then inserted about the first pin, and then the second alignment pin is inserted through the other guide block. The alignment pins thus assume an angle with respect to each other which corresponds to the angle set by the guide blocks on the arcuate track. The second pin is then inserted on through the guide block and into the bone on the other side of the position where the correction is to be made. The guide blocks and track are then removed from the pins with the pins remaining in the bone and with their distal ends protruding at an angle with respect to each other that corresponds to the desired angle of correction of the bone. The surgeon cuts through the bone at a position between the guide pins. The surgeon then derotates or aligns the segments of the bone until the alignment pins are parallel to each other. When the pins are parallel to each other the pins indicate to the surgeon that the desired derotation or realignment of the bone segments has been accomplished.

Thus, it is an object of this invention to provide an osteotomy guide for use by an orthopedic surgeon during the reorientation of the segments of a bone in a procedure for correcting a boney deformity, with the guide being simple in construction and reliable to use.

Another object of this invention is to provide a method and apparatus for realigning segments of a bone having an angular or rotational deformity.

Another object of this invention is to provide an osteotomy guide which is useful in aligning bone segments in both derotation procedures and alignment procedures.

Other objects, features and advantages of the present invention will become apparent upon reading the following specification, when taken in conjunction with the accompanying drawings.

BRIEF DESCRIPTION OF THE DRAWINGS

FIG. 1 is a perspective illustration of the osteotomy guide, showing the alignment pins inserted through the guide blocks of the guide and into bone segments.

FIGS. 2, 3 and 4 are schematic illustrations of bone correcting procedures.

FIG. 5 is a side cross-sectional view of the multiple pin guide block.

FIG. 6 is a front view of the multiple pin guide block with an alignment pin in place.

FIG. 7 is a back view of the multiple pin guide block with an alignment pin in place.

FIG. 8 is a top view of the multiple pin guide block.

FIG. 9 is a side cross-sectional view of the single pin guide block.

FIG. 10 is a front view of the single pin guide block with alignment pin in place.

FIG. 11 is a back view of the single pin guide block, with the holding plate removed therefrom.

FIG. 12 is a top view of the single pin guide block, with the holding plate and set screw shown in exploded relationship therewith.

FIG. 13 is a back view of the single pin guide block with the holding plate in position to close the pin opening.

FIG. 14 is a back view of the single pin guide block, similar to FIG. 13 but with the holding plate moved to the side to open the holding pin opening.

FIG. 15 is a cross-sectional view of a multiple pin guide block, showing an adaptor for use with a thin alignment pin.

DETAILED DESCRIPTION

Referring now in more detail to the drawings, in which like numerals indicate like parts throughout the several views, FIG. 1 illustrates the osteotomy guide 10 which includes an arcuate track 11 and first and second guide blocks 12 and 13. Alignment pins 15 and 16 are to be inserted through the guide blocks 12 and 13, as illustrated.

As illustrated in the lower portion of FIG. 1 and in FIGS. 2, 3 and 4, the alignment pins 15 and 16 are used to correct improper alignment of bones. For example, in a situation where a bone 18 is twisted or "malrotated" along its length, the orthopedic surgeon inserts pin 16 into the bone. The tip of the pin is sharp and has a shape suitable for drilling into the bone surface. The distal end of the pin 16 is mounted in a drill so that the pin can be rotated during the inserting procedure. After the pin 16 has been properly inserted in the bone 18, the osteotomy guide 10 is mounted to pin 16 by inserting the second guide block 13 about the pin 16. The alignment pin 15 is then inserted through its guide block 12, and the pin is rotated with the drill device as it penetrates bone 18. Both alignment pins should be inserted into the bone at an angle perpendicular to the longitudinal axis of the bone. When both pins 15 and 16 have been properly inserted in the bone 18, the osteotomy guide 10 is removed from the pins, the bone 18 is cut at 19 between the pins 15 and 16 with the cut also being formed at an angle perpendicular to the longitudinal axis of the bone, and as illustrated in FIG. 2, the bone segments 20 and 21 are rotated with respect to each other as indicated by arrows 22 and 24 until the pins 15 and 16 are parallel to each other, indicating that the bone segments have been derotated through the proper angle.

As illustrated in FIG. 3, when the longitudinal orientation of a bone 25 is to be adjusted, the alignment pins 15 and 16 are inserted in the bone segments 26 and 28 on opposite sides of the angle in the bone, with the pins located in a plane parallel to the longitudinal axis of the bone and defining an arc which corresponds to the angular deformity of the bone, and two cuts 29 and 30 are made between and parallel to alignment pins 15 and 16 so as to form a wedge-shaped segment 31 of the bone 25. The wedge-shaped segment is removed from between the segments 26 and 28 and the bone segments 26 and 28 are then moved as indicated by arrows 32 and 34 until alignment pins 15 and 16 are parallel to each other. This indicates that the cut ends of the bone segments 26 and 28 are parallel to each other.

As illustrated in FIGS. 1 and 5-8, guide block 12 is an approximately rectangular shaped structure in that it includes parallel top and bottom surfaces 35 and 36, back surface 38, side surfaces 39 and 40 and face 41. Side surfaces 39 and 40 are not parallel to each other, as will be explained in more detail hereinafter.

Face 41 has slot 42 formed therein. Slot 42 is of a width and depth that corresponds to the width and depth of arcuate track 11, so that the guide block 12 can be mounted on the arcuate track 11 by slipping the slot 42 about the track 11. Internally threaded set screw opening 44 extends through the top surface 35 of guide block 12 and intersects slot 42, and externally threaded set screw 45 is sized and shaped to be threaded through set screw opening 44. The set screw 45 is arranged to frictionally engage arcuate track 11 so as to rigidly hold guide block 12 to the arcuate track.

Guide block 12 is a multiple pin guide block in that it includes three parallel rectilinear guide pin openings 46, 47 and 48 extending therethrough, from top surface 35 to bottom surface 36. As illustrated in FIG. 8, the pin openings 46, 47 and 48 are located closely adjacent side surface 40 of the guide block. Internally threaded set screw bore 49 extends inwardly from back surface 38 into guide block 12 and intersects each of the guide pin openings 46, 47 and 48. Externally threaded set screw 50 is arranged to be threaded into set screw opening 49, and the end of the set screw 50 is to engage any pin present in any one of the openings 46, 47 or 48, to frictionally engage the pin and hold the pin in a rigid relationship with respect to the guide block 12.

As illustrated in FIGS. 9, 10, 11, 12, 13 and 14, the second guide block 13 is also approximately rectangular in shape and includes top and bottom surfaces 54 and 55, back surface 56, side surfaces 57 and 58 and face 59. Slot 60 is formed in face 59. Slot 60 also corresponds in width and depth to the width and depth of arcuate track 11 and is adapted to be slipped onto the end of the arcuate track 11 so that guide block 13 can be slipped along the length of the arcuate track 11. Internally threaded set screw opening 61 extends through top surface 54 and intersects slot 60, and externally threaded set screw 62 is sized and shaped to be threadedly received through set screw opening 61. Set screw 62 frictionally engages arcuate track 11 to rigidly mount second guide block 13 to the arcuate track.

Rectilinear groove 64 is formed in back surface 56 of guide block 13 and holding plate 65 is arranged to be positioned in flat abutment against back surface 56. Thus, holding plate 65 and the grooved back surface 56 together form an alignment pin opening through the guide block assembly 13. Internally threaded bores 67 and 68 are formed in back surface 56 of guide block 13 and connecting screws 69 and 70 are threaded into the bores 67 and 68. Holding plate 65 includes upper and lower cut outs or slots 71 and 72 at its top and bottom edges which form tabs 74, 75 at the top edge and tabs 76 and 77 at the bottom edge. The slots 71 and 72 are spaced apart a distance that corresponds to the spacing of bores 67 and 68 (FIG. 11). Thus, holding plate 65 can be placed in abutment with the grooved back surface 56 of guide block 13 and connecting screws 69 and 70 inserted in their threaded bores 67 and 68, and holding plate 65 will be maintained in position on the guide block 13.

Groove 64 of guide block 13 is shallower than the diameter of the alignment pin 16 and when the pin 16 is placed in the groove 64 and the holding plate 65 is tightly fastened to the guide block 13, the holding plate clamps the alignment pin in place. In addition, a set screw opening (not shown) can be formed in the holding plate 65 or in the guide block 13 so as to intersect groove 64, and a set screw (also not shown) can be threaded through the set screw opening to frictionally engage the alignment pin to hold it in place. With this construction, groove 64 is of a depth approximately equal to the diameter of guide pin 16, and guide pin 16 is slidable along the groove until the set screw is tightened.

The arrangement is such that when the connecting screws 69 and 70 are loosened, the holding plate 65 will be permitted to move away from the back surface 56 of guide block 13, and the slots 71 and 72 will permit the holding plate 65 to slide in its own plane to one side (FIG. 14) of the guide block 13. Since the bores 67 and 68 are located to one side of the guide block 13, holding plate 65 can be positioned so that its side edges are coextensive with the side surfaces 57 and 58 of guide block 13 (FIG. 13) or so that the holding plate 65 is slid out to the side and protrudes beyond the side surface 58 of the guide block 13, exposing groove 64, and the guide pin 16 can be removed from its groove 64.

Arcuate track 11 is constructed with a substantially constant radius of curvature. Alignment pin openings 46, 47 and 48 of multiple pin guide block 12 are oriented so that when guide block 12 is clamped to arcuate track 11 by set screw 45, the openings 46–48 extend parallel to the radius of curvature of arcuate track 11. Side surface 40 is also formed so that its extends parallel to the radius of curvature of arcuate track 11 when the guide block is fastened thereon by the set screw 45. Thus, guide block 12 is approximately wedge-shaped (FIGS. 6 and 7).

In a similar manner, guide block 13 is formed so that its groove 64 extends parallel to the radius of curvature of arcuate track 11 when guide block 13 is rigidly clamped to arcuate track 11 and side surface 57 adjacent groove 64 is parallel to the radius of curvature of the arcuate track. The corresponding side edge 78 of holding plate 65 is angled so as to be parallel to side surface 57 when holding plate 65 is in aligned overlying relationship with respect to guide block 13 (FIG. 13).

With this arrangement, guide blocks 12 and 13 can be moved toward abutment with each other and their facing side surfaces will move toward parallel abutment, with the bottom portions thereof not functioning to inhibit close positioning of the guide pins 15 and 16.

Guide marks 81 and 82 are formed on the face surfaces 41 and 59 of guide blocks 12 and 13, with the guide mark 81 being located in alignment with the openings 46, 47 and 48 of guide block 12 and with the guide mark 82 being located in alignment with slot 64 of guide block 13, so that the guide marks provide an indication of the location of the guide pins 15 and 16 on the scale 84 formed on the arcuate track 11. Scale 84 is formed in degrees about the center of curvature of the arcuate track. Thus, the guide blocks 12 and 13 with their guide marks 81 and 82 and arcuate track 11 with its scale 84 function as guide means for the placement of alignment pins 15 and 16.

Guide pins 15 and 16 have been illustrated as being of a diameter corresponding to the diameters of the guide pin openings 46–48; however, it will be understood that in some instances very small diameter guide pins 79 (FIG. 15) must be used. Thus, a tubular adapter 80 is threaded through the openings 46–48 or the groove 64 of the guide blocks 12 or 13, and a small diameter guide pin 79 is threaded through the opening of the tubular adapter. A set screw 81 can be used to rigidly fasten the small diameter guide pin 79 to the tubular adapter, and the tubular adapter is rigidly connected to the guide block by a set screw 50 (FIG. 5) or by the force applied by holding plate 65 against the guide pin present in groove 64 of guide block 13.

As illustrated in FIGS. 5 and 9, guide pin opening 47 is located a distance from slot 42 of guide block 12 a distance equal to the spacing of groove 64 from its slot 60 of guide block 13. Thus, if guide pins are inserted through guide pin opening 47 and through groove 64, the guide pins will be located at positions equally distant from arcuate track 11. However, guide pin openings 46 and 48 are positioned on opposite sides of guide pin opening 47 of guide block 12. Thus, if a guide pin is inserted through guide pin opening 46 or 48, that guide pin will be a distance from arcuate track 11 that is different from the distance of displacement of the guide pin inserted through groove 64.

When the osteotomy guide is to be utilized to derotate bone segments in the manner as illustrated in FIGS. 1 and 2, the guide pin 15 will be inserted through guide pin opening 46 or 48 of guide block 12 so that the guide pin 15 is off set longitudinally along the length of the bone 18 from guide pin 16. The longitudinal off set of the guide pins 15 and 16 permits the orthopedic surgeon to cut through the bone 18 at a right angle with respect to the longitudinal axis of the bone. After the alignment pins have been inserted into the bone, the osteotomy guide is removed from the alignment pins 15 and 16, by loosening holding plate 65 from guide block 13 and sliding the holding plate to one side so that the groove 64 is open, and by loosening the set screw 50 of the other guide block 12 and slipping that guide block off the distal end of the alignment pin 15. The surgeon is then able to cut the bone between the alignment pins and manipulate the limb of the patient so as to derotate the bone segments 20 and 21 with respect to each other until the alignment pins 15 and 16 are parallel to each other.

When an alignment correction is to be made to a bone as illustrated in FIGS. 3 and 4, it is important that the tips of the alignments pins 15 and 16 be inserted through the bone segments 26 and 28 so that the tips of the alignment pins substantially merge together on the opposite side of the bone. This permits a small wedge-shaped segment 31 to be removed from the bone 25. In order to be assured that the alignment pins 15 and 16 will merge on the opposite side of the bone, the surgeon will experiment with the osteotomy guide prior to the pin insertion procedure, by inserting the alignment pins 15 and 16 through the guide blocks 12 and 13 to determine how far the pins should be inserted through the guide blocks before their tips merge. The surgeon notes the amount that the distal ends of the alignment pins protrude through the top surfaces of the guide blocks 12 and 13 before he begins the bone alignment procedures.

After the surgeon has inserted alignment pin 16 in the bone 25, he feels the opposite side of the bone to determine the degree of penetration of the alignment pin, and adjusts the depth of penetration of the alignment pin until it is determined that the pointed portion of the alignment pin has just broken the surface of the remote side of the bone. The osteotomy guide is then inserted on the alignment pin 16 with the top surface 54 of the guide block 13 positioned exactly at the predetermined location along the length of the alignment pin 16, and then the connecting screws 69 and 70 are tightened so as to rigidly hold the guide block 13 in place. Then the second alignment pin 15 is inserted through its guide pin opening 47 and the drill device utilized to rotate alignment pin 15 and to cause the alignment pin to penetrate bone 25 until only the predetermined length of the guide pin protrudes from the top surface 35 of guide block 12. The surgeon then understands that the tips of the alignment pins 15 and 16 are substantially merged at the opposite side of the bone 25. Cuts 29 and 30 are then made through the bone 25 parallel to the alignment pins 15 and 16 and transverse to the length of the bone and the small wedge-shaped bone segment 31 is removed from between the bone segments 26 and 28.

While this invention has been described in specific detail with particular reference to a preferred embodiment thereof, it will be understood that variation and modifications can be effected within the spirit and scope of the invention as described hereinbefore and as defined in the appended claims.

I claim:

1. An osteotomy guide comprising an arcuate track of a substantially constant radius, a pair of guide blocks movable along the length of said arcuate track, each of said guide blocks defining at least one rectilinear pin opening therethrough extending parallel to the radius of said arcuate track for receiving rectilinear pin members therethrough and for holding the pin members parallel to the radius of curvature of said track, one of said guide blocks including a plurality of said pin openings with one of the plurality of pin openings being displaced from the arcuate track a distance substantially equal to the displacement of the pin opening of the other guide block from the arcuate track, with a second one of the plurality of pin openings being displaced from the arcuate track a distance greater than the displacement of the pin opening of the other guide block from the arcuate track, and with a third one of the plurality of pin openings being displaced from the arcuate track a distance less than the displacement of the pin opening of the other guide block from the arcuate track, connecting means for rigidly holding said guide blocks to said arcuate track, means for rigidly holding a pin in a pin opening of said one of said guide blocks comprising a set screw opening intersecting the plurality of said pin openings of said one guide block and a set screw for extending into said set screw opening, said arcuate track including a scale extending therealong which indicates angles thereabout with respect to the center of its radius of curvature, whereby a first pin is inserted through a bone, a pin opening of one of the guide blocks is inserted about the protruding end of the first pin, and a second pin is inserted through a pin opening of the other guide block and then into the bone at an angle with respect to the first pin which corresponds to the angle between the pin openings of the guide blocks on the arcuate track.

2. The osteotomy guide of claim 1 and wherein the surfaces of said guide blocks which face each other are formed in a plane approximately parallel to the radius of curvature of the arcuate track, and wherein said pin openings of said guide blocks are positioned closer to the facing surfaces of the guide blocks than to the oppositely facing surfaces thereof.

3. The osteotomy guide of claim 1 and wherein said guide blocks each define a track slot therethrough of a width and depth corresponding to the width and depth of said arcuate track, with the track slot of each guide block inserted about said arcuate track, and wherein said connecting means comprises a set screw opening extending through each guide block and intersecting the track slot, and a set screw extending through each set screw opening for engagement with said arcuate track.

4. An osteotomy guide comprising an arcuate track of a substantially constraint radius, a pair of pin guide means mounted on and movable along said arcuate track, one of said pin guide means including means for holding a pin parallel to a radiant of said arcuate track at a first distance from said arcuate track and the other one of said pin guide means including means for holding a pin parallel to a radiant of said arcuate track at variable distances from said arcuate track which are equal to or different from said first distance, at least one of said pin guide means including means for releasing its pin laterally with respect to the length of its pin so that the pin guide means is not required to move along the length of the pin to release the pin, a scale imposed on the arcuate track which indicates the angles thereabout with respect to its center of curvature, whereby a first pin is inserted into a bone, one of the pin guide means mounted to the first pin, a second pin is mounted in the second pin guide means and is moved along its length and inserted into the bone at an angle with respect to the first pin which corresponds to the angle between the pair of pin guide means as indicated by the scale on the arcuate track, and after both pins are inserted in the bone the arcuate track and pin guide means are removed from the pins.

5. The osteotomy guide of claim 4 and wherein said other one of said pin guide means includes means for holding a pin at three positions, with one position at a distance from said arcuate track which is less than the distance of the pin in the other pin guide means from the arcuate track, with a second position at a distance from said arcuate track equal to the distance of the pin in the other pin guide means from said arcuate track, and with a third position at a distance from said arcuate track which is greater than the distance of the pin in the other guide means from said arcuate track.

6. An osteotomy guide comprising an arcuate track of a substantially constant radius, a pair of guide blocks movable along the length of said arcuate track, each of said guide blocks defining at least one rectilinear pin opening therethrough extending parallel to the radius of said arcuate track for receiving rectilinear pin members therethrough, connecting means for rigidly holding said guide blocks to said arcuate track, means for rigidly holding a pin in a pin opening of at least one of said guide blocks, the pin opening of at least one of said guide blocks being formed by a groove in a surface of the guide block, and a holding plate for extending over said groove in abutment with the grooved surface of the guide block, and connecting means for holding said holding plate in flat slidable abutment with the grooved surface of said guide block whereby the holding plate is slidable between a position over the groove and a position where the groove is not covered by the holding plate, said arcuate track including a scale extending therealong which indicates angles thereabout with respect to the center of its radius of curvature, whereby a first pin is inserted through a bone, a pin opening of one of the guide blocks inserted about the protruding end of the first pin, and a second pin is inserted through the pin opening of the other guide block and then into the bone at an angle with respect to the first pin openings of the guide blocks on the arcuate track.

* * * * *